United States Patent [19]
Richardson

[11] 4,144,255
[45] Mar. 13, 1979

[54] SUBSTITUTED (PHENYLENEDIMETHYLENE)DIAMINES

[75] Inventor: Kenneth Richardson, Canterbury, England

[73] Assignee: Pfizer Inc., New York, N.Y.

[21] Appl. No.: 815,915

[22] Filed: Jul. 15, 1977

Related U.S. Application Data

[60] Division of Ser. No. 720,146, Sep. 3, 1976, Pat. No. 4,058,562, which is a division of Ser. No. 611,856, Sep. 10, 1975, Pat. No. 4,003,929, which is a continuation-in-part of Ser. No. 543,824, Mar. 11, 1975, abandoned.

[51] Int. Cl.$^2$ .......................... C09F 5/00; C11C 3/00
[52] U.S. Cl. ........................... 260/404.5; 260/501.17; 424/324
[58] Field of Search ..................... 260/404.5 R, 562 R, 260/501.17, 501.2; 424/320, 324

[56] References Cited

U.S. PATENT DOCUMENTS 3,789,073  1/1974  Narayanan et al. ............. 260/558 A
3,872,171  3/1975  Cronin et al. .................... 260/584 R Primary Examiner—John Niebling
Attorney, Agent, or Firm—Connolly and Hutz

[57] ABSTRACT

Novel diamines containing an aromatic nucleus which are useful as antiviral agents in vertebrates are disclosed.

6 Claims, No Drawings

SUBSTITUTED (PHENYLENEDIMETHYLENE)DIAMINES

CROSS REFERENCE TO RELATED APPLICATIONS

This application is a division of application Ser. No. 720,146 filed Sept. 3, 1976, and now U.S. Pat. No. 4,058,562 which, in turn, is a division of application Ser. No. 611,856 filed Sept. 10, 1975 and now U.S. Pat. No. 4,003,929, which, in turn, is a continuation in part of Ser. No. 543,824, filed Mar. 11, 1975, and now abandoned.

BACKGROUND OF THE INVENTION

The present invention relates to the preparation of novel diamine antiviral agents containing an aromatic nucleus and their use as prophylactic and therapeutic agents in vertebrates. It is believed that these compounds function as endogeneous interferon inducers though the observed activity of these compounds is in no way predictated on this mechanistic interpretation. A discussion of the background of this art is given in the commonly assigned application, Ser. No. 330,042, filed Feb. 6, 1973 now U.S. Pat. No. 3,872,171 the disclosure of which is incorporated here by reference.

SUMMARY OF THE INVENTION

According to the present invention, effective antiviral activity is shown by novel amines having the general structural formula

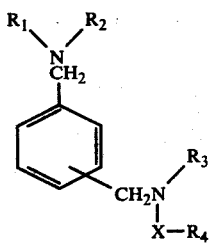

and their pharmaceutically acceptable acid addition salts;

$R_1$ is selected from the group consisting of hydrogen, methyl and 2-hydroxyethyl;

$R_2$ is selected from the group consisting of hydrogen, lower alkyl and w-hydroxy lower alkyl;

$R_3$ is selected from the group consisting of alkyl having from 12 to 24 carbon atoms, a monovalent aliphatic non-cyclic hydrocarbon having from 12 to 24 carbon atoms and from one to two double bonds therein,

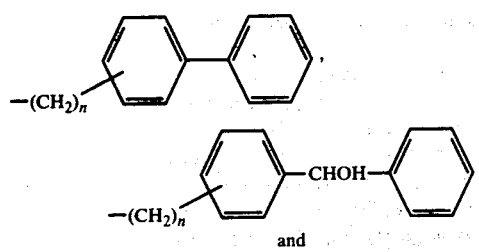

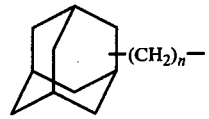

wherein n is an integer from one to six;

X is selected from the group consisting of

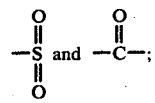

and $R_4$ is selected from the group consisting of alkyl having from 12 to 24 carbon atoms, a monovalent aliphatic non-cyclic hydrocarbon having from 12 to 24 carbon atoms and from one to two double bonds therein, w-hydroxy lower alkyl, phenyl, naphthyl, phenylnaphthyl and phenylalkyl having up to three carbon in the alkyl moiety.

Preferred compounds are those in which $R_1$ and $R_2$ are both hydrogen, those in which $R_3$ contains from 14 to 20 carbon atoms, those in which $R_3$ is normal alkyl and those in which $R_3$ is n-tetradecyl, n-hexadecyl and n-octadecyl and particularly preferred.

Among the various phenylene isomers, the 1,3-isomer is preferred and the sulfone group is the preferred choice for X. Compounds in which $R_4$ is normal alkyl, contains from 14 to 20 carbon atoms, contains an even number of carbon atoms or is 2-naphthyl are preferred. Also preferred are compounds in which $R_3$ and $R_4$ are identical. Of special preference are those compounds in which $R_3$ and $R_4$ are both n-hexadecyl and n-octadecyl.

Particular compounds which constitute the preferred embodiment of the present invention are exemplified below and pharmacological test data are given for them.

The antiviral agents of the present invention serve both a therapeutic and prophylactic function. They may be administered parenterally, intranasally or topically. Dosage ranges are given below.

By pharmaceutically acceptable acid addition salts is meant those salts which are non-toxic at the dosages administered. The acid addition salts of the above-mentioned bases which may be employed are the water-soluble and water-insoluble salts such as the hydrochloride, hydrobromide, phosphate, nitrate, sulfate, acetate, mesylate, hexafluorophosphate, citrate, gluconate, benzoate, propionate, butyrate, sulfosalicylate, maleate, laurate, malate, fumarate, succinate, oxalate, tartrate, amsonate (4,4'-diaminostilbene-2,2'-disulfonate), pamoate (1,1'-methylene-bis-2-hydroxy-3-naphthoate), stearate, 3-hydroxy-2-naphthoate, p-toluenesulfonate, picrate, lactate and suramin salt.

The term alkyl as used herein includes both unbranched and branched moieties. The term lower alkyl includes all such radicals containing up to six carbon atoms.

DETAILED DESCRIPTION OF THE INVENTION

The compounds described herein exhibit broad spectrum activity against a variety of viruses in vivo when administered parenterally (subcutaneously, intramuscularly, intraperitoneally) intranasally (e.g. by inhalation or spray), or topically to vertebrate animals. This usefulness is primarily one of prophylactic rather than of therapeutic control of virus infections. Although the present invention is not to be construed as limited by such a theory, it is possible that the compounds of this invention function in combating viral infections by virtue of their ability to induce the production of endogenous interferon. They induce interferon in vivo, but they cannot do so directly in cell cultures. They, therefore, can be considered as stimulators of host defense mechanisms.

Further, these compounds stimulate the animal body to produce interferon when administered alone or in combination with an otherwise inactive substance, for example, single-stranded ribonucleic acid, such as highly polymerized ribonucleic acid from yeast, yeast nucleic acid (Calbiochem 55712, Calbiochem, Los Angeles, California). Those compounds which induce interferon when administered alone are given at considerably lower doses when given in combination with the single-stranded ribonucleic acid or other such material.

Compounds of the present invention are prepared by contacting the appropriate a-bromo-tolunitrile with a substantially equimolar amount of an amine of the formula $R_3NH_2$ in reaction-inert solvent such as chloroform at ambient temperature until the reaction is substantially complete. Reaction-inert solvents are those which are substantially free of adverse effects on reactants and products under the conditions employed. The crude intermediate is isolated as a semi-solid by filtering and evaporating the reaction mixture. It may be purified by numerous methods known to those skilled in the art such as silica gel chromatography. The intermediate, an N-$R_3$-α-aminotolunitrile, is then contacted in reaction-inert solvent such as methylene chloride at about ambient temperature with a compound chosen from the group consisting of those of the structure $R_4$—(C+O)—Cl and $R_4$—(O+S+O)-Cl until the reaction is substantially complete. The reaction mixture is then washed with water, dried and evaporated to an oil which may be purified by chromatographic means. The di-N-substituted-α-aminotolunitrile is then dissolved in a reaction-inert solvent such as substantially anhydrous tetrahydrofuran and contacted with at least an equivalent amount of borane dissolved in a reaction-inert solvent at approximately ambient temperature under an inert atmosphere until the reaction is substantially complete. The reaction mixture is then filtered and evaporated to afford the crude product as an oil which is purified by silica gel chromatography.

Acid addition salts of the compounds described herein are prepared by conventional procedures as by mixing the amine compound in a suitable solvent with the required acid and recovering the salt by evaporation or by precipitation by addition of a non-solvent for the salt. Hydrochloride salts are readily prepared by passing dry hydrogen chloride through a solution of the amine compound in an organic solvent such as ether.

The antiviral activity of the above-described materials is determined by the following procedure. The test compound is administered to mice by the intraperitoneal route eighteen to twenty-four hours prior to challenging the mice with a lethal dose of encephalomyocarditis virus and determining the survival rate ten days after challenge. The procedure in which the drug is given eighteen to twenty-four hours before and at a distinctly different site from virus injection is designed to eliminate local effects between drug and virus and select only compounds which product a systemic interferon response.

Antiviral activity was determined as follows. Groups of 10 female albino mice (20-25g) were given single intraperitoneal injections of the compounds tested, or no treatment, on the day preceeding a lethal virus challenge. The challenge virus was the EMC strain of encephalomyocarditis virus (17th passage in this laboratory), prepared as a 20% brain suspension in Hank's Balanced Salt Solution. Infectivity by the subcutaneous (sc) route in mice was $10^6$ $LD_{50}/0.2ml$ (the $LD_{50}$ was determined as the challenge dose causing death in 50% of the animals after 10 days. The viral challenge used in these experiments (20-30 $LD_{50}$ in 0.2 ml, sc) caused paralysis and death in the majority of unprotected mice between 3-5 days after infection. Antiviral activity was expressed as the relative survival ($S_r$) in experimental groups compared to the untreated controls on the 10th day after challenge. Survival in the control group was generally 10% or less. $S_r$ values greater than 20 are considered indicative of antiviral. $S_r$ is defined as $$S_r = \frac{(\%S_x - \%S_e) + 10/N[(\Sigma s_x)_{1-10} - (\Sigma s_e)_{1-10}]}{(100 - \%S_e) + 10/N[(\Sigma N)_{1-10} - (\Sigma s_e)_{1-10}]} \times 100$$

where:
$S_r$ = Relative Survival
%S = Percent Survival after 10 days
N = Number of Mice/Group
x = Experimental Group
e = EMC Control Group
s = Number of Survivors (on a given day)
1-10 = Days 1 through 10 After Challenge The results of the challenge are given in Table I below.

TABLE I

| | X | R$_1$ | R$_2$ | R$_3$ | R$_4$ | 50 | 15 | 5 | 1.5 | No. of Experiments |
|---|---|---|---|---|---|---|---|---|---|---|
| | | | | | | | $S_r$ at indicated dosage (mg/kg) | | | |
| 1,3-phenyl | —SO$_2$— | H | H | C$_{18}$H$_{37}$ | C$_{16}$H$_{33}$ | 86 (2) | 85 | 32 | 16 | (4) |
| 1,3-phenyl | —SO$_2$— | H . | H | C$_{18}$H$_{37}$ | 2-naphthyl | 90 (2) | 65 | 44 | 37 | (4) |

The test compounds are administered alone and in combination with from about 2 to about 20 times by weight of an otherwise inactive (non-inducer of interferon and nonantiviral), single-stranded, highly polymerized ribonucleic acid from yeast, yeast nucleic acid.

Parenteral, topical and intranasal administration of the above described amines to an animal, including man, before exposure of the animal to an infectious virus provide rapid resistance to the virus. The resistance engendered is non-specific and is effective against a great number of viruses. Such administration is effective when given as much as five days prior to exposure to the virus. Preferably, however, administration should take place from about three days to about one day before exposure to the virus, although this will vary somewhat with the particular animal species and the particular infectious virus. The compounds of the present invention may be employed effectively in a range of from 0.1 to 20 mg/kg body weight on a daily basis and a preferred range is from 0.1 to 5.0 mg/kg body weight.

When administered parenterally, the materials of this invention are used at a level of from about 0.1 mg/kg of body weight to about 20 mg/kg of body weight. The favored range is from about 0.1 mg/kg to about 5.0 mg/kg of body weight. The dosage, of course, is dependent upon the animal being treated and the particular amine compound involved and is to be determined by the individual responsible for its administration. Generally, small doses will be administered initially with gradual increase in dosage until the optimal dosage level is determined for the particular subject under treatment.

Intramuscular injections are the preferred method of parenteral injection for several reasons such as simplicity and convenience. Vehicles suitable for parenteral injection may be either aqueous such as water, isotonic saline, isotonic dextrose, Ringer's solution or non-aqueous such as fatty oils of vegetable origin (cottonseed oil, peanut oil, corn, sesame) and other non-aqueous vehicles which will not interfere with the efficacy of the preparation and are non-toxic in the volume or proportion used (glycerol, ethanol, propylene, glycol, sorbitol.) Additionally, compositions suitable for extemporaneous preparation of solutions prior to administration may advantageously be made. Such compositions may include liquid diluents, for example, propylene, glycol, diethyl carbonate, glycerol and sorbitol.

When the materials of this invention are administered, they are most easily and economically used in a dispersed form in an acceptable carrier. When it is said that this material is dispersed, it means that the particles may be molecular in size and held in true solution in a suitable solvent or that the particles may be colloidal in size and dispersed through a liquid phase in the form of a suspension or an emulsion. The term "dispersed" also means that the particles may be mixed with and spread throughout a solid carrier so that the mixture is in the form of a powder or dust. This term is also meant to encompass mixtures which are suitable for use as sprays, including solutions, suspensions or emulsions of the agents of this invention.

In practicing the intranasal route of administration of this invention any practical method can be used to contact the inducer with the respiratory tract of the animal. Effective methods include administration of the inducer by intranasal or nasopharyngeal drops and by inhalation as delivered by a nebulizer or an aerosol. Such methods of administration are of practical importance because they provide an easy, safe and efficient method of practicing this invention. For intranasal administration of the inducer, usually in an acceptable carrier, a concentration of inducer between 0.1 mg/ml and 20 mg/ml is satisfactory and convenient.

For topical application the inducers are most conveniently used in an acceptable carrier to permit ease and control of application and better absorption. Here also concentrations in the range of from about 0.1 mg/ml to about 20 mg/ml are satisfactory. In general, in the above two methods of administration a dose within the range of about 0.1 mg/kg to about 20 mg/kg of body weight and, preferably, from about 0.1 mg/kg to about 5.0 mg/kg of body weight will be administered.

The compounds employed in this invention may be employed alone i.e., without other medicinals, as mixtures of more than one of the herein-described compounds or in combination with other medicinal agents, such as analgesics, anesthetics, antiseptics, discongestants, antibiotics, vaccines, buffering agents and inorganic salts, to afford desirable pharmacological properties. Further, they may be administered in combination with hyaluronidase to avoid, or at least, to minimize local irritation and to increase the rate of absorption of the compound. Hyaluronidase levels of at least about 150 (U.S.P.) units are effective in this respect although higher or lower levels can, of course, be used.

Those materials of this invention which are water-insoluble including those which are of low and/or difficult solubility in water, are, for optimum results, administered in formulations, e.g., suspensions, emulsions, which permit formation of particle sizes of less than about $20\mu$. The particle sizes of the formulations influence their biological activity apparently through better absorption of the active materials. In formulating these materials various surface active agents are the partial esters of common fatty acids, such as lauric, oleic, stearic, with hexitol anhydrides derived from sorbitol, and the polyoxyethylene derivative of such ester products. Such products are sold under the trademarks "Spans" and "Tweens," respectively, and are available from the Atlas Powder Co., Wilmington, Delaware. Cellulose ethers, especially cellulose methyl ether (Methocel, available from the Dow Chemical Co., Midland, Michigan) are highly efficient as protective colloids for use in emulsions containing the materials of this invention.

In some cases, the compositions of the present invention are desirably administered by aerosol spray. For such application, a halogenated hydrocarbon propellant of up to 2 carbon atoms is employed. The propellant may be any of the conventional propellant used in aerosol formulations, for example halogenated hydrocarbon of the fluorohydrocarbon or fluorohalohydrocarbon type such as trichloromonofluoromethane, dichlorodifluoromethane, dichlortetrafluoroethane, monochlorotrifluoromethane, monochlorodifluoromethane and mixtures of any of these together or with other propellants. Typical of suitable propellants are those disclosed in, for example, U.S. Pat. No. 2,868,691 and sold under the trademark Freon The examples to follow are illustrative and in no way limit the scope of the appended claims.

EXAMPLE I

N-(n-Octadecyl)-N-(n-Hexadecylsulfonyl)-1,3-Phenylenedimelhylene)Diamine

Octadecylamine (61.2 g.) and α-bromo-m-tolunitrile (25.47 g.) in chloroform (1100 ml.) were stirred at room temperature for 5 hours. The reaction mixture was filtered and filtrate was evaporated to leave a yellow semi-solid. This was dissolved in chloroform and chromatographed on a silica-gel column (500 ml.) by eluting with chloroform (1600 ml.) followed by ethyl acetate (1800 ml.). The ethyl acetate eluates were combined and evaporated to leave an oil which solidified to give the product (19.5 g.).

This nitrile (7.0 g.) and triethylamine (2.03 g.) in methylene dichloride (100 ml.) was treated with hexadecylsulfonyl chloride (6.5 g.). This solution was stirred at room temperature for 16 hours and then filtered. The filtrate was washed with water (2 × 100 ml.), dried (sodium sulfate) and evaporated to an oil. This oil was chromatographed on a "dry-column" of silicage (16 inches × 2 inches diameter) with elution by chloroform. That part of the column corresponding to Rf=0.2–0.6 was separated from the rest and the product washed off with chloroform. The washings were dried (sodium sulfate) and evaporated to yield an oil (5.0 g.)

This nitrile (1.0 g.) dissolved in dry tetrahydrofuran (20 ml.) was treated with borane in tetrahydrofuran (1.5 ml. of 1 Molar) and this reaction mixtures was stirred at room temperature under nitrogen for 2 hours. A further portion of borane in tetrahydrofuran (0.5 ml. of 1 molar) was added and the mixture was stirred under nitrogen at room temperature for 3 days. Ethanol (10 ml.) was added and the mixture was filtered and evaporated to leave an oil. This oil was chromatographed on a dry-column of silica-gel (15 inches × 1 inch diameter) with elution by benzene/ethanol (4/1). Fractions corresponding to $R_f 5 = 0.6-0.9$ were removed from the rest and eluted with ethyl acetate These eluates were evaporated to leave an oil. This was dissolved in diethyl ether and HCl gas was bubbled in, and evaporation left the hydrochloride, a tan solid (390 mg). The structure was confirmed by nuclear magnetic resonance spectroscopy.

The analogous 2-naphthylsulfonyl compound was made in a similar manner except that hexadecylsulfonyl chloride was replaced by 2-naphthalenesulfonyl chloride.

The structure of the final product was confirmed by nuclear magnetic resonance spectroscopy.

In a similar fashion, the following compounds may be prepared

| Y | Y | $R_1$ | $R_2$ | $R_3$ | $R_4$ |
|---|---|---|---|---|---|
| 1,3-phenyl | —SO$_2$— | H | H | n-hexadecyl | n-octadecyl |
| " | " | H | H | " | n-tetradecyl |
| " | " | H | H | " | n-hexadecyl |
| " | " | H | H | n-octadecyl | n-tetradecyl |
| 1,3-phenyl | " | H | H | n-hexadecyl | 2-naphthyl |
| 1,4-phenyl | " | H | H | " | " |
| 1,3-phenyl | " | H | H | n-tetradecyl | " |
| 1,3-phenyl | $\overset{O}{\underset{\|}{-C-}}$ | H | H | n-octadecyl | n-hexadecyl |
| " | " | H | H | " | 2-naphthyl |
| 1,3-phenyl | " | H | H | n-hexadecyl | n-octadecyl |
| " | " | H | H | " | n-tetradecyl |
| " | " | H | H | " | n-hexadecyl |
| " | " | H | H | n-octadecyl | n-tetradecyl |
| " | " | H | H | n-hexadecyl | 2-naphthyl |
| 1,4-phenyl | " | H | H | " | " |
| 1,3-phenyl | " | H | H | n-tetradecyl | " |

What is claimed is:

1. A compound of the structure

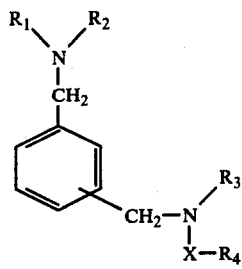

and its pharmaceutically acceptable acid addition salts wherein
$R_1$ and $R_2$ are both hydrogen,
$R_3$ and $R_4$ are each alkyl of from 14 to 20 carbon atoms and
X is

2. A compound of claim 1 wherein $R_3$ and $R_4$ are each normal alkyl of from 14 to 20 carbon atoms.

3. A compound of claim 1 wherein $R_3$ and $R_4$ each contains an even number of carbon atoms.

4. A compound of claim 1 wherein $R_3$ and $R_4$ are identical.

5. A compound of claim 1 wherein the phenylene group is meta-phenylene.

6. A compound of claim 5 wherein $R_3$ and $R_4$ are each selected from the group consisting of n-hexadecyl and n-octadecyl.

* * * * *